(12) United States Patent
Bolstad et al.

(10) Patent No.: US 11,594,300 B2
(45) Date of Patent: Feb. 28, 2023

(54) VITERBI DECODER FOR MICROARRAY SIGNAL PROCESSING

(71) Applicant: AFFYMETRIX, INC., Carlsbad, CA (US)

(72) Inventors: Benjamin Bolstad, Kensington, CA (US); Alan Roter, Healdsburg, CA (US); Radharani Duttagupta, Foster City, CA (US)

(73) Assignee: AFFYMETRIX, INC., Carlsbad, CA (US)

( * ) Notice: Subject to any disclaimer, the term of this patent is extended or adjusted under 35 U.S.C. 154(b) by 293 days.

(21) Appl. No.: 16/755,925

(22) PCT Filed: Oct. 17, 2018

(86) PCT No.: PCT/US2018/056294
§ 371 (c)(1),
(2) Date: Apr. 14, 2020

(87) PCT Pub. No.: WO2019/079455
PCT Pub. Date: Apr. 25, 2019

(65) Prior Publication Data
US 2020/0294621 A1 Sep. 17, 2020

Related U.S. Application Data

(60) Provisional application No. 62/573,568, filed on Oct. 17, 2017.

(51) Int. Cl.
*G16B 25/00* (2019.01)
*G16B 50/00* (2019.01)

(52) U.S. Cl.
CPC ............. *G16B 25/00* (2019.02); *G16B 50/00* (2019.02)

(58) Field of Classification Search
None
See application file for complete search history.

(56) References Cited

U.S. PATENT DOCUMENTS

| 2009/0098547 A1 | 4/2009 | Ghosh |
| 2011/0207612 A1 | 8/2011 | Park et al. |
| 2011/0301854 A1* | 12/2011 | Curry ..................... G16B 20/20 |
| | | 702/19 |

FOREIGN PATENT DOCUMENTS

| WO | WO-2013075000 A1 | 5/2013 |
| WO | WO-2016187051 A1 | 11/2016 |

OTHER PUBLICATIONS

International Search Report and Written Opinion for Application No. PCT/US2018/056294, dated Jan. 29, 2019, 14 pages.
Vinson J.P., et al., "Comparative Gene Prediction using Conditional Random Fields", Dec. 4, 2006 (Dec. 4, 2006), XP055541057, 8 pages, retrieved from the Internet: URL:http://papers.nips.cc/paper/2966-comparative-gene-prediction-using-conditional-random-fields.pdf.
Wang K., et al., "Copy Number Variation Detection via High-Density SNP Genotyping", Cold Spring Harbor Protocols, vol. 3, No. 6, Jun. 1, 2008 (Jun. 1, 2008), XP055541046, 7 Pages, DOI: 10.1101/pdb.top46.

* cited by examiner

*Primary Examiner* — Hung Q Dang

(57) ABSTRACT

A system and method for region-based calling utilizes a probability distribution of a phi-transformed logarithmic ratio to determine a set of possible transition paths through markers and marker states, constructs a local evidence matrix for each of the markers and generates a total per-marker value for each segment in a discrete region.

10 Claims, 12 Drawing Sheets

```
/*Receives regions which may be defined by chromosome, start, end position and number of
markers and outputs the summarized log ratio and total information content with the
chromosome, start, end position. Three state model is used, (gain, loss, neutral) so
each vector of means is 3 entries long. Call type is -1 for loss, 0 for neutral, 1 for
gain*/
forEach(region){
    phiTransformLR();
    CRF(phiAdjustedLR, meansAssociatedWithEachState, perMarkerVariabilityParam,
transitionMatrix, DegreesOfFreedomForControllingEmissionDistributions,
initialStateProbabilities, stateVector);
/*
inputs: phiAdjustedLR, meansAssociatedWithEachState, perMarkerVariabilityParam,
transitionMatrix, DegreesOfFreedomForControllingEmissionDistributions,
initialStateProbabilities
Outputs: stateVector
*/
initialSegmentation(stateVector,initialSegmentation);
    //inputs: stateVector
    //Outputs: initialSegmentation
cleanupSegmentation(initialSegmentation,minimumSegmentSize,reducedSegmentationTab
le);
    //inputs: initialSegmentation, minimumSegmentSize
    //Outputs: reducedSegmentationTable
finalizeOutputSegmentation(reducedSegmentationTable,finalTable);
    //inputs: reducedSegmentationTable
    //Outputs: finalTable
```

FIG. 8

```
/*CRF subroutine*/
CRFSubroutine( phiAdjustedLR, meansAssociatedWithEachState,
perMarkerVariabilityParam, transitionMatrix, dOFForCtrlEmissDist,
initialStateProbabilities){
    determineEmissionProbabilities(){
        forEach(marker){
            forEach(state in marker){
                tDist = (marker.phiAdjLR - marker.stateMean) /
                marker. varEstimate(i,k);
                emissionProb = emissionProb(tDist(dOFForCtrlEmissDist));
            }
        }
    }
    computeLocalEvidence(emissionProb){
    /*Determine for each state at each marker index the level of evidence for that state based on
    the observed data. Segments must be a minimum of Ncrf markers long, local window will be
    2Ncrf-1 markers in length. Find the most likely configuration passing though each marker
    index for each state such that the path length is Ncrf markers or longer. TransitionMatrix is a
    diagonally-weighted transition matrix (ie stay in same state), giving probabilities for
    transitioning from one state to another. Entry i,j is probability of transition from state i to
    state j.
    */
    standardizedProbabilityOfPathP = (probabilityAtMarkers(emissionProb));
    transitionMatrix= maximize(emissionProb);
    Return transitionMatrix;
```

FIG. 8 (continued)

```
};
findMostLikelyPath(transitionMatrix, localEvidenceMatrix,
initialProbabilityVector){
/*initialProbabilityVector is a vector giving the initial probability of being in
each state*/
    viterbi(transitionMatrix, localEvidenceMatrix, initialProbabilityVector){
    /*Sum of logs is used to avoid numerical underflow. The description here
    assumes that state labels are consecutive integers 1,...,Nstates*/
        transitionMatrix1[state, 1] = log(IP[state]) +
        log(localEvidenceMatrix[state,1])
        transitionMatrix2[state, 1] = 0
        //initialization phase
        for( state in states){
            Set transitionMatrix1[state, 1] = log(IP[state]) +
            log(localEvidenceMatrix[state, 1])
            Set transitionMatrix2[state, 1] = 0
        }
        //forward pass
        for (observations in markers){
            for(state in 1,...,Nstates){
                /*Find k that maximizes
                findKMax(transitionMatrix1[k,observation-1] +
                log(transitionMatrix[k,state]))
                transitionMatrix1[state, obs] =
                log(localEvidenceMatrix[state,observation] +
                transitionMatrix1[k,observation-1] +
```

FIG. 8 (continued)

```
                log(transitionMatrix[k,state])
            transitionMatrix2[state,observation] = k
        }
    }
    //backtracking
    findKMax(transitionMatrix1[k, Nmarkers])
    prev_state=k
    S[Nmarkers] = prev_state
    for(obs= Nmarkers,...,2){
        prev_state = transitionMatrix2[prev_state,obs]
        S[obs-1]=prev_state
    }
    forEach(marker){
        /*this is a vector or states assigned to each marker by
        following the maximal path through data and is N-markers long*/
        return: mostLikelyStateAssociatedWithEachMarker;
    }
};

initialSegementation(mostLikelyStateAssociatedWithEachMarker){
    //Input: State Vector as produced by Viterbi
```

FIG. 8 (continued)

```
for(stringOfContguousMarker in mostLikelyStateAssociatedWithEachMarkers){
    initialSegmentatinTable.addStringAsSegment();
}
/*An initial segmentation consisting of a list of start and stop indices and
states.*/
return initialSegmentationTable
}
cleanupSegmentation(initialSegmentationTable, minSegmentSize){
    /*Input: Initial Segmentation Table. Minimum segment size.
    Output: Reduced Segmentation Table.
    for(segment in initialSegmentationTable){
        If segment < minSegmentSize{
            mergedSegment = segment.mergewithneighbor().
            reducedSegmentationTable.add(mergedSegment)
        }
    }
    return reducedSegmentationTable;
}
finalizeOutputSegmentation(reducedSegmentationTable){
    for(segment in reducedSegmentationTable){
        /*Summarize ph-adjusted LR within segment using median*/
        segment.convertToGenomicPosition()
        segment.ph-adjustedLogRatio.summarize(median); within segment using median
    }
    return: per-markerInformationContent;
}
return: final table;
```

FIG. 8 (continued)

VITERBI DECODER FOR MICROARRAY SIGNAL PROCESSING

RELATED APPLICATION

This application is a U.S. 35 § 371 National Phase Application of International Application Number PCT/US2018/056294 filed on 17 Oct. 2018, which claims the benefit of U.S. Provisional Application No. 62/573,568 filed 17 Oct. 2017, each of which is hereby incorporated by reference in its entireties.

BACKGROUND

There is mounting evidence for the importance of exon-level copy number changes in a number of pathologies, including neurodevelopmental disease, with up to 40% of intragenic mutations involving just one or two exons within a gene. Microarray-based comparative genomic hybridization allows for a high-resolution evaluation of DNA copy number alterations associated with chromosomal abnormalities. In this approach, DNA samples are hybridized to targets on a solid plate or platform, and probes which are built to scan a specific part to the genome deliver an intensity value which is then read by a computing device which makes a call.

SUMMARY

In one aspect, a discrete region-based calling method is provided. The method may include receiving a region delineated by a chromosome, a start marker and an end marker and for each marker within the region: dividing a logarithmic ratio for the marker by an expected responsiveness to copy number change to generate a phi-transformed logarithmic ratio; modeling a probability distribution of the phi-transformed logarithmic ratio in one or more of states by calculating an emission probability for each of the states; translating a local path window across the marker to determine a set of possible transition paths through the states and the markers; constructing a local evidence matrix, for each of the markers, including a level of evidence for each of the states based on the observed data; operating a Viterbi decoder with a transition matrix, the local evidence matrix and a state initial probability vector to generate a state vector including the state associated with each of the markers along the most probable path through the local evidence matrix; operating a first segmenter with the state vector to partition segments into a segmentation table of contiguous markers with the same state; operating a second segmenter with the segmentation table and a minimum segment size to merge segments below the minimum segment size into adjoining segments to produce a minimized segmentation table; operating a segmentation finalizer on the minimized segmentation table to convert segment indexes to genomic positions; and summarizing the phi-transformed logarithmic ratio within each segment using the segment's median; and generating a total per-marker value for each segment.

In some embodiments, the transition matrix is symmetric and a probability of remaining in the same state is higher than transitioning to a different state.

In some embodiments, the state initial probability vector further includes the initial probability of the marker being in each of the states.

In some embodiments, the local path window length is one less than twice the length of the examined segment.

In some embodiments, the local evidence matrix dimensions are controlled by the states for rows and the markers for columns.

In some embodiments, calculating the emission probability for each of the states further includes subtracting the mean for the state from the phi-transformed logarithmic ratio and dividing by a variability estimate the marker for the state.

In some embodiments, the logarithmic ratio includes a $\log_2$ ratio.

In some embodiments, the logarithmic ratio is the logarithm of the intensity of a specific probe set on an array divided by a reference intensity.

In some embodiments, the reference intensity is the average intensity of the intensities observed for the specific probe set from different arrays, where the different arrays are hybridized to nucleic acid populations derived from different individuals.

In some embodiments, the probe set includes a set of probes configured to hybridize to the same genomic or transcriptomic locus.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 8 illustrates a process for making region-based calls in accordance with one embodiment.

DETAILED DESCRIPTION

Figure 1:
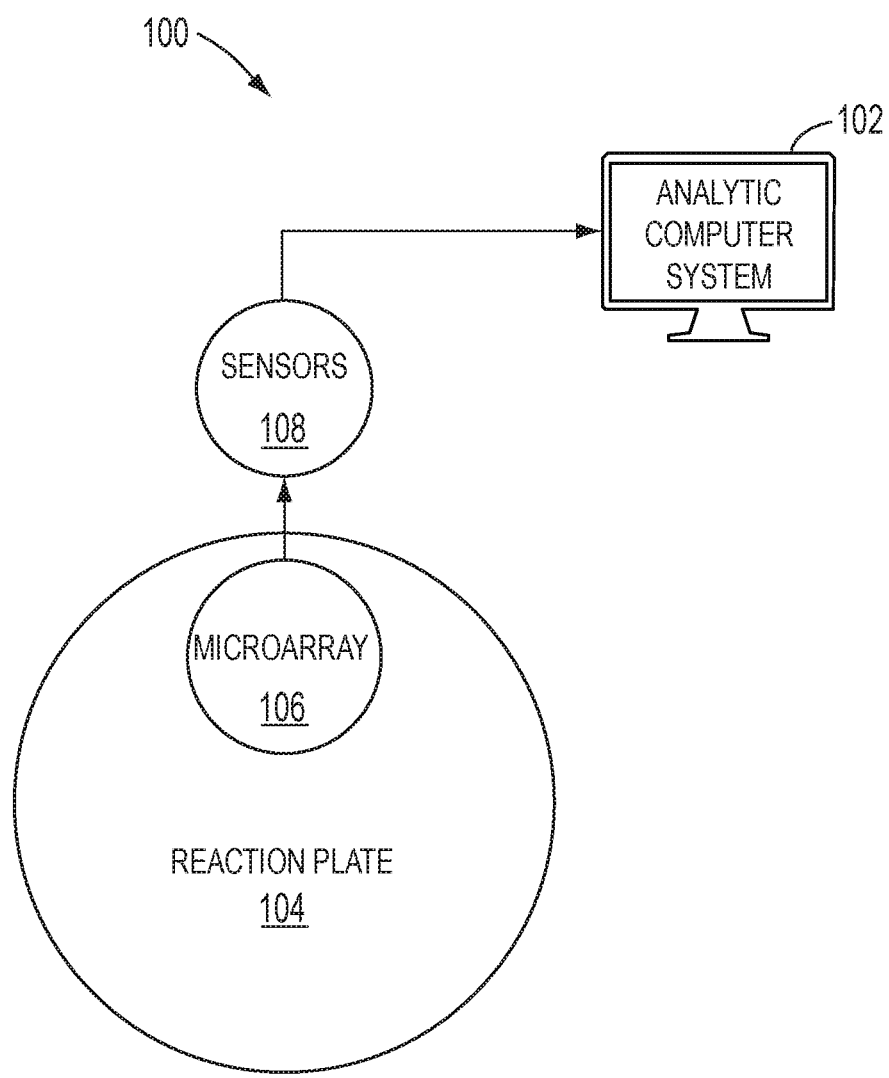
FIG. 1 illustrates a system for genotyping copy number variants 100 in accordance with one embodiment.

Copy Number Variants (CNVs) in predefined regions are frequently surveyed within Genome-Wide Association Studies (GWAS) performed on the basis of microarray genotyping data. Methods for detection of abnormalities must provide good coverage of individual exons in addition to high resolution, and high throughput. However, efficient, accurate and high throughput determination of copy number states with microarray data remains difficult to achieve.

In order to provide copy number analysis with improved efficiency and accuracy, especially under a high throughput setting, embodiments of a system and method are disclosed that employ a three-state conditional random field model to describe the observed logarithmic ratio data over a discrete region. In some embodiments, for each region, the most probable path states are found based on the observed logarithmic ratio, and a per-region segmentation is generated based on this information. A callable region may be a contiguous set of markers, where each marker is within 500 base pairs of its neighbors, and the region overlaps with an exon. In some embodiments, each marker is within 10, 50, 100, 150, 200, 250, 300, 350, 400, 450, 500, 550, 600, 650, 700, 750, 800, 850, 900, 950, 1,000 or more base pairs or any number of base pairs between the foregoing values. A callable region may also incorporate more than one exon, and likewise it is possible for a large exon to span more than one region.

In some embodiments, segments only fall within regions, so that there is no joining of segments between regions. In some embodiments, for each marker, the phi-transformation is generated by dividing the measure associated with the marker's expected responsiveness to copy number change, with a higher value indicating more responsiveness. These values may be provided as precomputed inputs.

In some embodiments, utilizing a Linear Chain Conditional Random Field Model (CRF) allows for all observed data to be utilized when determining hidden states, instead of only viewing each observation one at a time. The state at time point i may be based on data x and state at timepoint i-1, instead of determining the state at time point i based only on data $x_i$ and state at timepoint i-1, as with a Hidden Markov Model. Emission probabilities are modeled through a t-distribution of phi-adjusted log ratios in each state.

In some embodiments, local evidence is computed, and a Viterbi decoder is utilized to find the most likely path through the data.

$i$ = marker index $k$ = state for $k = 1$ $\sigma_{ik}$ = variability estimate for marker $i$ in state $k_i$ $u_k$ = mean for each state $df$ = degrees of freedom of $t$ – distribution $t_{ik} = \dfrac{y_i - \mu_k}{\sigma_{ik}}$ Suppose that f is the t-distribution pdf with df degrees of freedom, then the emission probability is $p_{ik}=f(t_{ik})$ in some embodiments. In some of such embodiments, the mean for each of the state parameters is provided as a parameter input to the algorithm. The $\sigma_i$ parameters are estimated using a combination of sigma base and sigma multiplier in some embodiments. For a given marker, in some embodiments:

$\sigma_i$=sigma base+sigma multiplier*max(1,7.5*MAPD) *MarkerLRMAD where MarkerLRMAD is a measure of variability associated with each marker, and where the sigma multiplier is a non-negative floating point number used in computation of variability component of emission probability distributions. The sigma base is a non-negative floating point number used in computation of variability component of emission probability distributions in certain embodiments.

In some embodiments, for each state at each marker index, the level of evidence for the state at a given marker index is based on the observed data in a small window surrounding that location. In some embodiments, segments must be a minimum of $N_{crf}$ markers long, and the local window will be $2(N_{crf}-1)$ markers in length. In some embodiments, the most likely configuration is found by passing through each marker index for each state such that the path length is $N_{crf}$ markers or longer. In some embodiments, if $E_{ik}$ is the local evidence at marker i for state k, and $E_{ik}p$ is the standardized probability of path p, then:

$E_{ik}=E_{ik}=_p \max E_{ikp}$

For example if there are N markers (in the region), and k states, then the goal is the production of the local evidence matrix:

$$\begin{bmatrix} E_{11} & \cdots & E_{N1} \\ \vdots & \ddots & \vdots \\ E_{1K} & \cdots & E_{NK} \end{bmatrix}$$

In some embodiments, the Viterbi decoder receives a transition matrix which gives the probabilities for transitions from one state to another. For example, entry i,j is the probability of transitioning from state i to state j. The Viterbi decoder may employ a "sum of logs" approach to avoid numerical undertow. The transition matrix generated by the Viterbi decoder may be a symmetric matrix with most of the probability on the diagonal (i.e. within a same state). The transition matrix may be parameterized by a single parameter which gives the probability of staying in same state. This probability can be given to the diagonal entries of the transition matrix. The remaining entries of each row may be given the remaining probability split equally.

For example, for a three state model with transition diagonal 0.995 the transition matrix would be:

$$\begin{bmatrix} .995 & .0025 & .0025 \\ .0025 & .995 & .0025 \\ .0025 & .0025 & .995 \end{bmatrix}$$

During initial segmentation, a state vector is received from the Viterbi decoder, and may contain start and stop indexes as well as a specified state.

In some embodiments, during cleanup segmentation, the initial segmentation table is transformed into a reduced segmentation table by merging small segments with their neighbors. This may be implemented in a recursive manner and processes only the first small segment (if there are multiple small segments) before beginning recursion. Recursion is ended when there are no more small segments to process. If a small segment falls between two segments which agree on a state, then all three segments are merged together (and take on the state of the two neighbors) at least in some embodiments. If the small segment falls between two segments differing in state, then the small segment joins the larger (in marker count) of the two segments (and lose their state in favor of the state of the longer segment) in certain embodiments. If the small segment falls between two segments differing in state, and the two adjoining segments are of the same size the small segment joins the first segment (and loses its state in favor of the first segment) in some embodiments.

"GeneCalling" in this context refers to: an open-platform mRNA transcriptional profiling technique. The GeneCalling protocol measures levels of cDNA, which are correlated with gene expression levels of specific transcripts.

"Genetic marker" in this context refers to: a gene or DNA sequence with a known location on a chromosome that can be used to identify individuals or species. It may be described as a variation (which may arise due to mutation or alteration in the genomic loci) that may be observed. A genetic marker may be a short DNA sequence, for example, a sequence surrounding a single base-pair change (single nucleotide polymorphism, SNP), or a long one. Some commonly used types of genetic markers are: RFLP (or Restriction fragment length polymorphism) SSLP (or Simple sequence length polymorphism) AFLP (or Amplified fragment length polymorphism) RAPD (or Random amplification of polymorphic DNA) VNTR (or Variable number tandem repeat) SSR Microsatellite polymorphism, (or Simple sequence repeat) SNP (or Single nucleotide polymorphism) STR (or Short tandem repeat) SFP (or Single feature polymorphism) DArT (or Diversity Arrays Technology) RAD markers (or Restriction site associated DNA markers).

"φ" (sometimes "anglicized" to "phi") in this context is used to indicate that each marker has specific parameterization to adjust for responsiveness to copy number change and typical variability.

"State Initial Probabilities" in this context refers to: a vector giving initial probability of being in each state.

"State Vector" in this context refers to: a vector of states assigned to each marker by following the maximal path through the data.

Referring to FIG. 1, a system for genotyping copy number variants 100 according to some embodiments comprises an analytic computer system 102, a reaction plate 104, sensors 108, and a microarray 106.

In some embodiments, the analytic computer system 102 receives data from the sensors 108. The sensors 108 may be optical sensors to detect fluorescence from the microarray 106 on the reaction plate 104.

Figure 2:
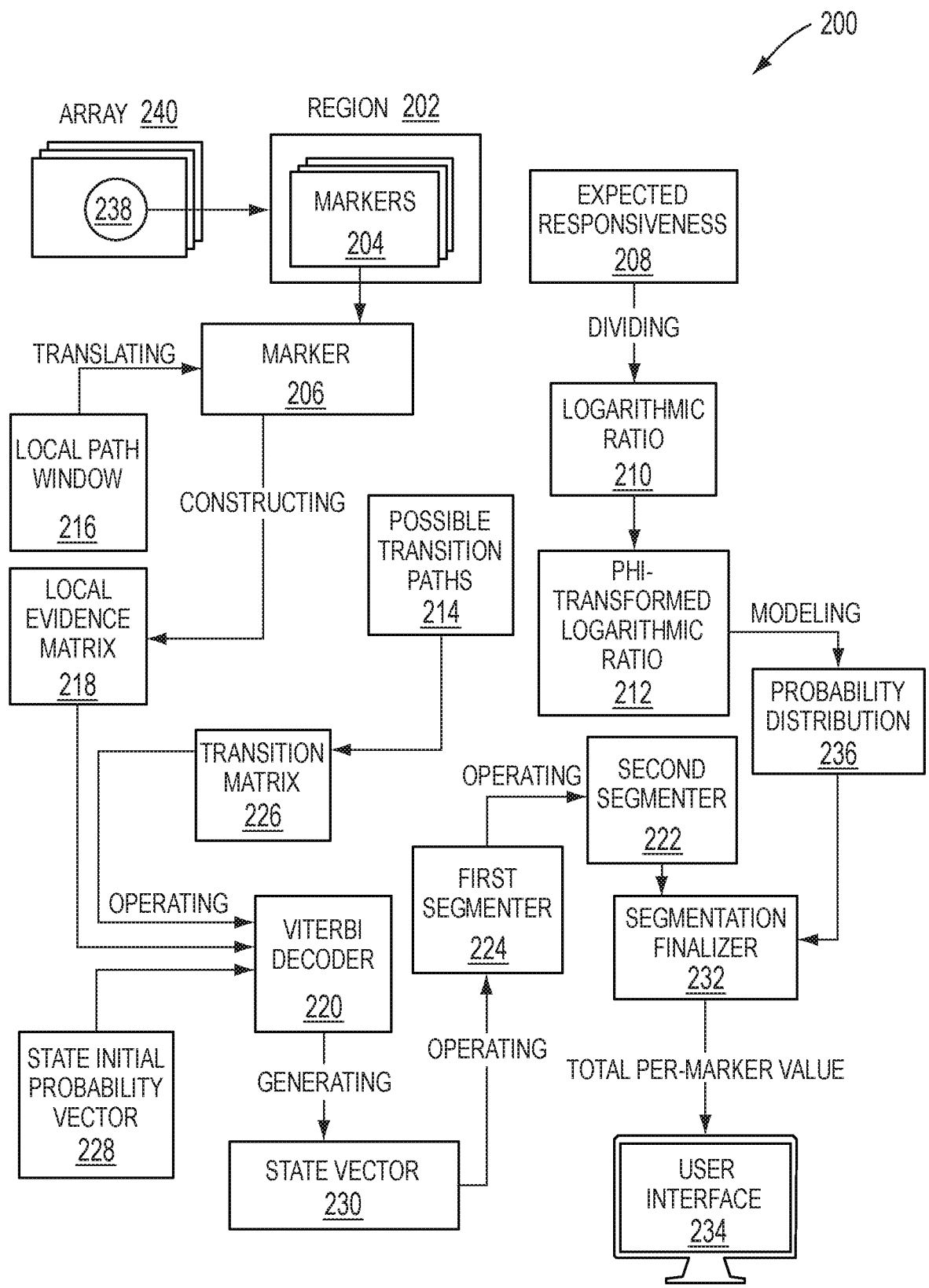
FIG. 2 illustrates a system for making region-based calls 200 in accordance with one embodiment.

Referring to FIG. 2, a system for making region-based calls 200 according to some embodiments comprises a region 202, markers 204, a marker 206, an expected responsiveness 208, a logarithmic ratio 210, a phi-transformed logarithmic ratio 212, a possible transition paths 214, a local path window 216, a local evidence matrix 218, a Viterbi decoder 220, a second segmenter 222, a first segmenter 224, a transition matrix 226, a state initial probability vector 228, a state vector 230, a segmentation finalizer 232, a user interface 234, a probability distribution 236, a sensor 238, and an array 240.

In some embodiments, the sensor 238 transmits a signal containing data regarding region 202 from the sensor 238 which reads an emission from the array 240. The logarithmic ratio 210 may be divided by the expected responsiveness 208 to generate a phi-transformed logarithmic ratio 212. The probability distribution 236 of the phi-transformed logarithmic ratio 212 for each state may be modeled by calculating an emission probability for each of the states. Marker 206 may be selected from the markers 204 and the local path window 216 may be translated across the marker 206 to determine the possible transition paths 214, constructing a local evidence matrix 218 for the marker 206. In some embodiments, the Viterbi decoder 220 is operated with the transition matrix 226, the local evidence matrix 218 and the state initial probability vector 228 to generate the state vector 230.

In some embodiments, the state vector 230 operates the first segmenter 224 to partition segments into a segmentation table of contiguous markers with the same state. The first segmenter 224 may operate the second segmenter with the segmentation table and a minimum segment size to merge segments below the minimum segment size into adjoining segments to produce a minimized segmentation table. The second segmenter 222 may operate the segmentation finalizer 232 on a minimized segmentation table to convert segment indexes to genomic positions, summarize the phi-transformed logarithmic ratio within each segment using the segment's median, and generate a total per-marker value for each segment. The per-marker value is displayed on the user interface 234 in some embodiments.

Figure 3:
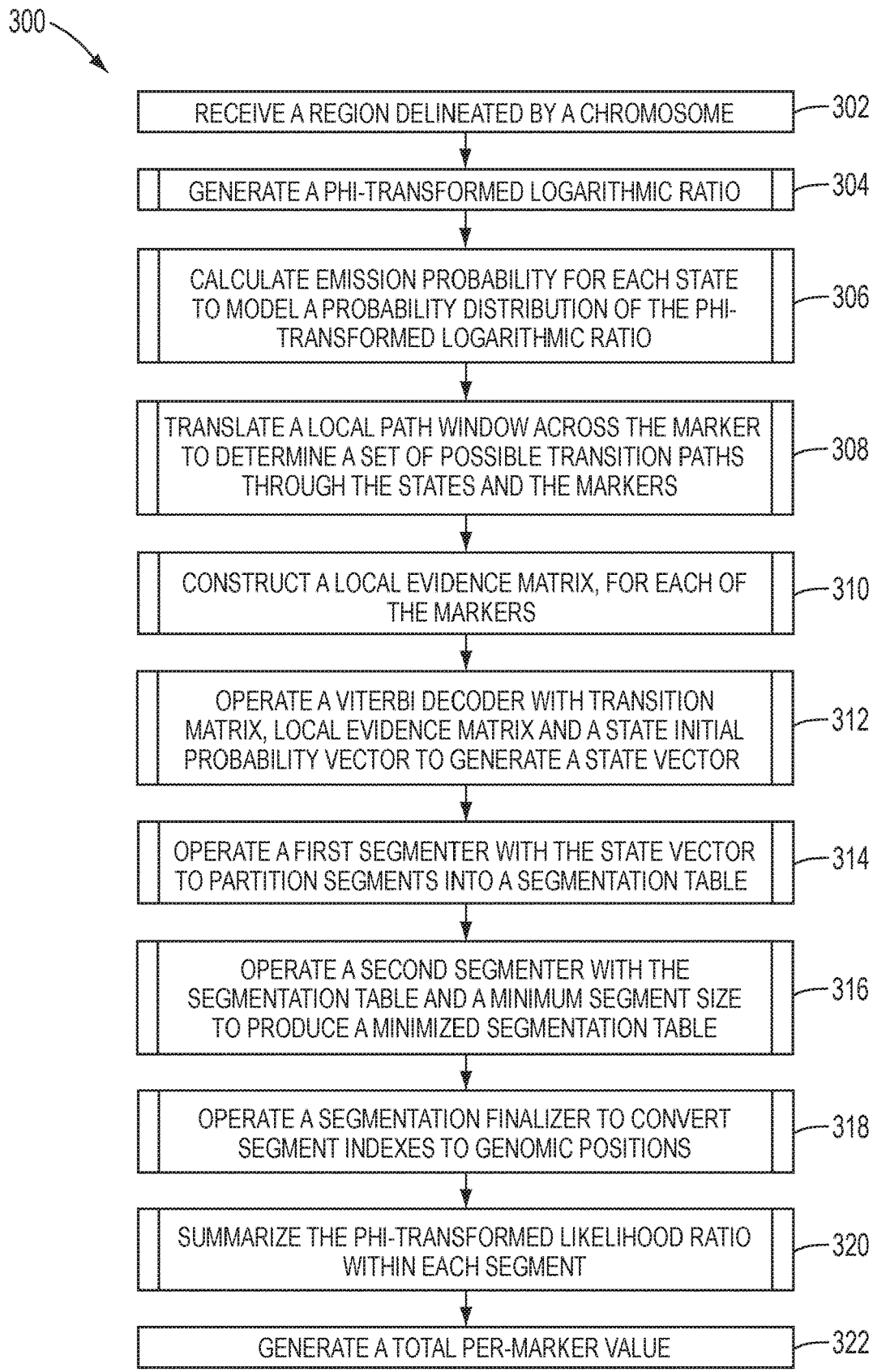
FIG. 3 illustrates an embodiment of a process for making region-based calls 300.

In some embodiments, the system for making region-based calls 300 may be operated in accordance with the process outlined in FIG. 3.

Referencing FIG. 3, the process for making region-based calls 300 receives a region delineated by a chromosome, a start marker and an end marker (block 302). In some embodiments, one or more additional steps can be performed before, after or between any steps illustrated in various embodiments of figures herein. In addition, one or more steps shown in the exemplary embodiments of the figures can be omitted to the extent that would not substantially reduce the functionality of the assay.

In some embodiments, the process 300 divides a logarithmic ratio for a marker by an expected responsiveness to copy number change to generate a phi-transformed logarithmic ratio (subroutine block 304).

In some embodiments, the process 300 calculates a probability distribution of the phi-transformed logarithmic ratio in each state by calculating an emission probability for each of the states (subroutine block 306).

In some embodiments, the process 300 translates a local path window across the marker to determine a set of possible transition paths through the states and the markers (subroutine block 308).

In some embodiments, the process 300 constructs a local evidence matrix, for each of the markers, comprising a level of evidence for each of the states based on the observed data (subroutine block 310).

In some embodiments, the process 300 operates a Viterbi decoder with a transition matrix, the local evidence matrix and a state initial probability vector to generate a state vector comprising the state associated with each of the markers along the most probable path through the local evidence matrix (subroutine block 312).

In some embodiments, the process 300 operates a first segmenter with the state vector to partition segments into a segmentation table of contiguous markers with the same state (subroutine block 314).

In some embodiments, the process 300 operates a second segmenter with the segmentation table and a minimum segment size to merge segments below the minimum segment size into adjoining segments to produce a minimized segmentation table (subroutine block 316).

In some embodiments, the process 300 operates a segmentation finalizer on the minimized segmentation table to convert segment indexes to genomic positions (subroutine block 318).

In some embodiments, the process 300 summarizes the phi-transformed logarithmic ratio within each segment using the segment's median (subroutine block 320).

In some embodiments, the process 300 generates a total per-marker value for each segment (block 322).

According to one aspect of the disclosure, a discrete region-based calling method may include receiving a region delineated by a chromosome, a start marker and an end marker and for each marker within the region, and may divide a logarithmic ratio for the marker by an expected responsiveness to copy number change to generate a phi-transformed logarithmic ratio. The method may model a probability distribution of the phi-transformed logarithmic ratio in each state by calculating an emission probability for each of the states, and translate a local path window across the marker to determine a set of possible transition paths through the states and the markers. The method may then construct a local evidence matrix, for each of the markers, which may include a level of evidence for each of the states based on the observed data. The method may then operate a Viterbi decoder with a transition matrix, the local evidence matrix and a state initial probability vector to generate a state vector may include the state associated with each of the markers along the most probable path through the local evidence matrix. A first segmenter may be operated with the state vector to partition segments into a segmentation table of contiguous markers with the same state. A second segmenter may be operated with the segmentation table and a minimum segment size to merge segments below the minimum segment size into adjoining segments to produce a minimized segmentation table. A segmentation finalizer may be operated on the minimized segmentation table to convert segment indexes to genomic positions. The phi-transformed logarithmic ratio may be summarized within each segment using the segment's median. The transition matrix may be symmetric and a probability of remaining in the same state is higher than transitioning to a different state. The state initial probability vector may further include the initial probability of the marker. In some embodiments, the state initial probability vector may be in each of the states. The local path window length may be one less than twice the length of the examined segment. The local evidence matrix dimensions may be controlled by the states for rows and the markers for columns. Calculating the emission probability for each of the states may further include subtracting the mean for the state from the phi-transformed logarithmic ratio and dividing by a variability estimate the marker for the state. A total per-marker value for each segment may then be generated for each segment.

Figure 4:
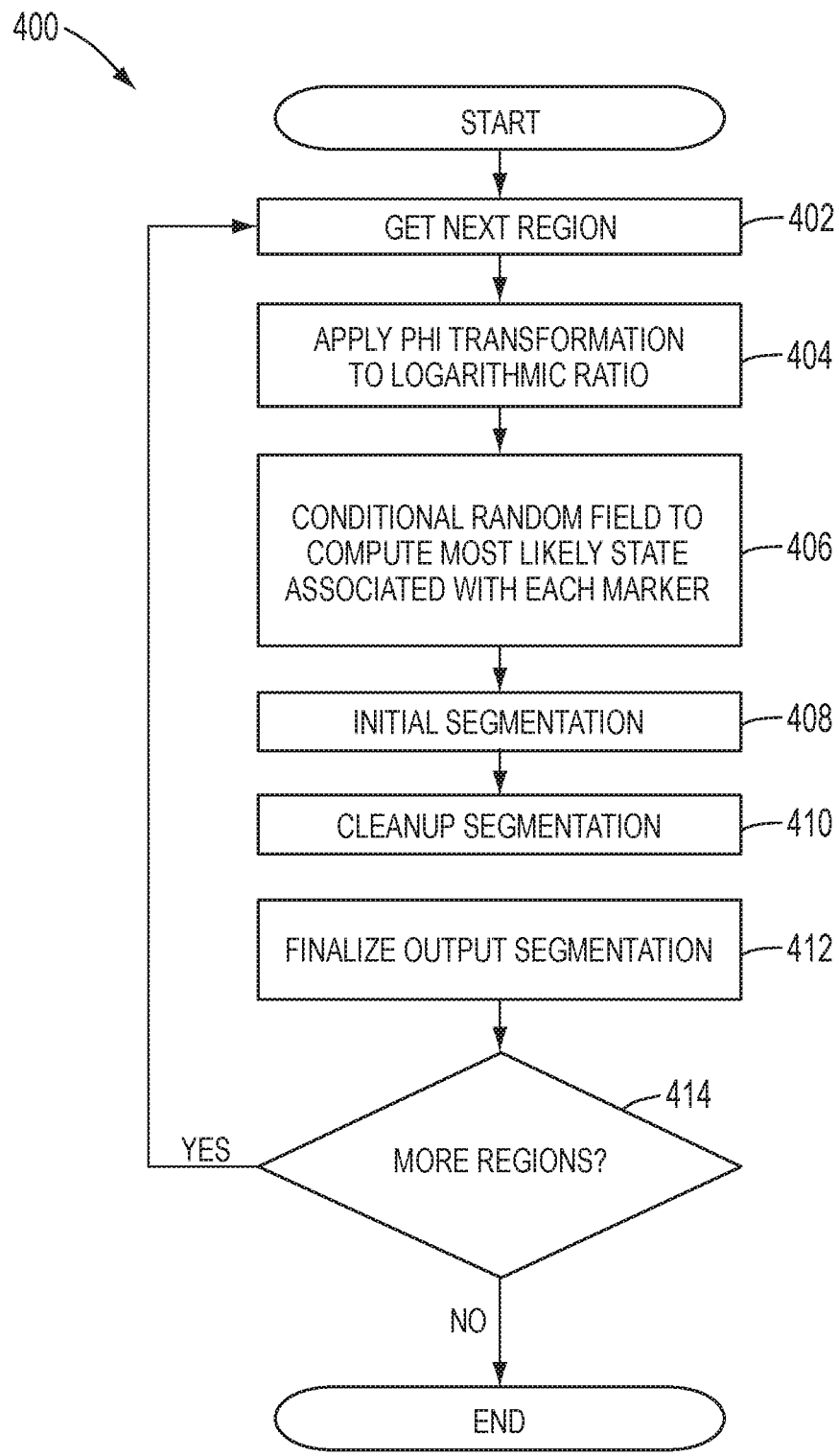
FIG. 4 illustrates further aspects of a process for making region-based calls 400 in accordance with one embodiment.

Referring to FIG. 4, a process for making region-based calls 400 according to some embodiments retrieves the next region (block 402). The process 400 may generate a phi-transformed logarithmic ratio (block 404), executes a conditional random field-based process to compute the most likely state associated with each marker (block 406), and may initiate initial segmentation wherein each string of contiguous markers with same state becomes a segment (block 408).

In some embodiments, the process for making region-based calls 400 then initiates cleanup segmentation to remove small segments by merging them with their neighbors (block 410), and finalizes output segmentation, converting segment indexes to genomic positions, summarizing the phi-adjusted logarithmic ratio within each segment using the median, and providing per-marker information content (block 412). The process 400 may check for more regions and repeats if more regions are found, otherwise, the process ends (decision block 414). A more detailed embodiment of the process 400 is provided in FIG. 8.

Figure 5:
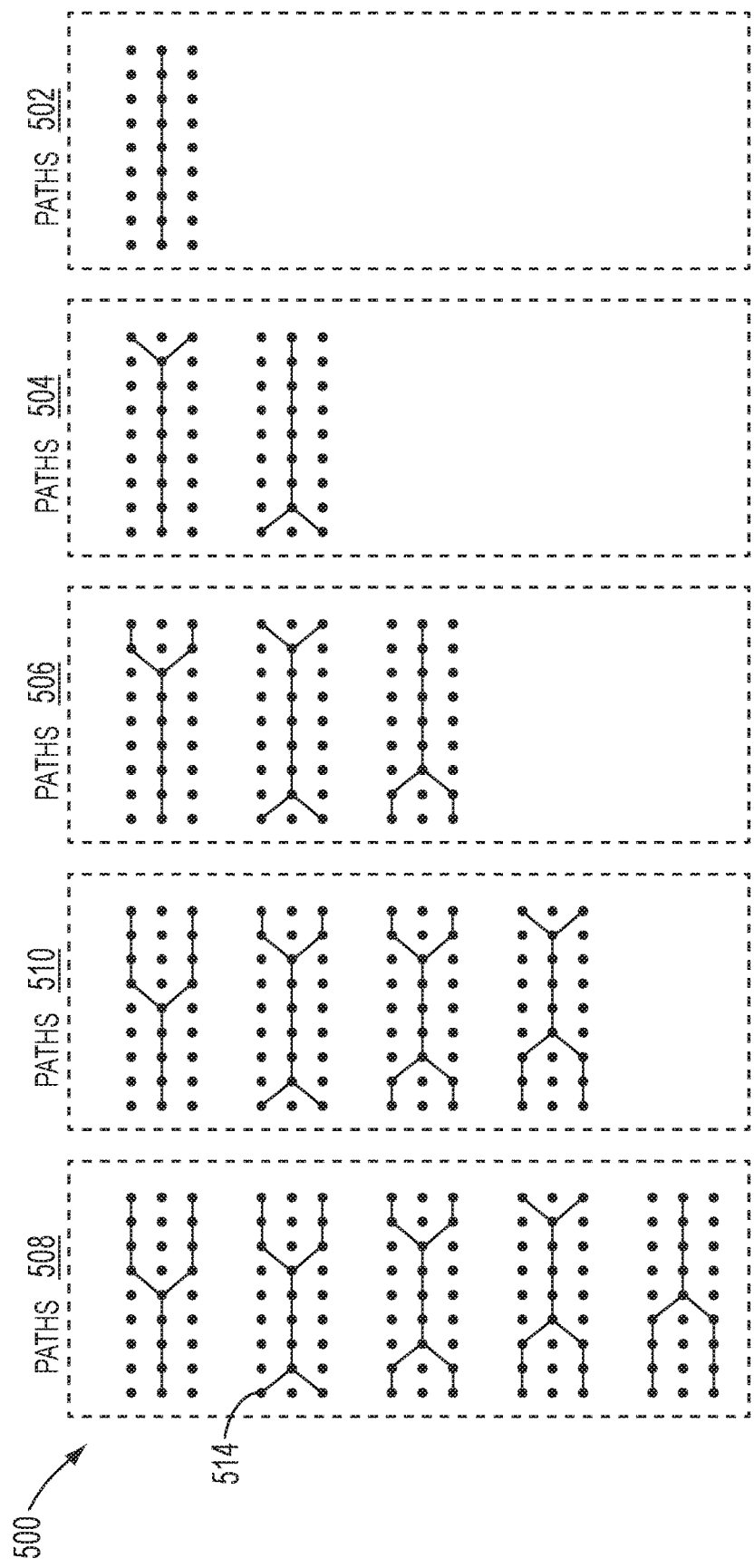
FIG. 5 illustrates local evidence paths 500 in accordance with one embodiment.

Referring to FIG. 5, an example of local evidence paths 500 according to some embodiments comprise paths 502, paths 504, paths 506, paths 508, paths 510, an emission probability matrix 512, a path 514, a path probability 516, and a standardized path probability 518.

In some embodiments, paths 508 have length 5. Paths 510 may have length 6. Paths 506 may have length 7. Paths 504 may have length 8. Paths 502 may have length 9. The path 514 in the paths 508 may have corresponding properties of path probability 516, standardized path probability 518, and emission probability matrix 512.

Figure 6:
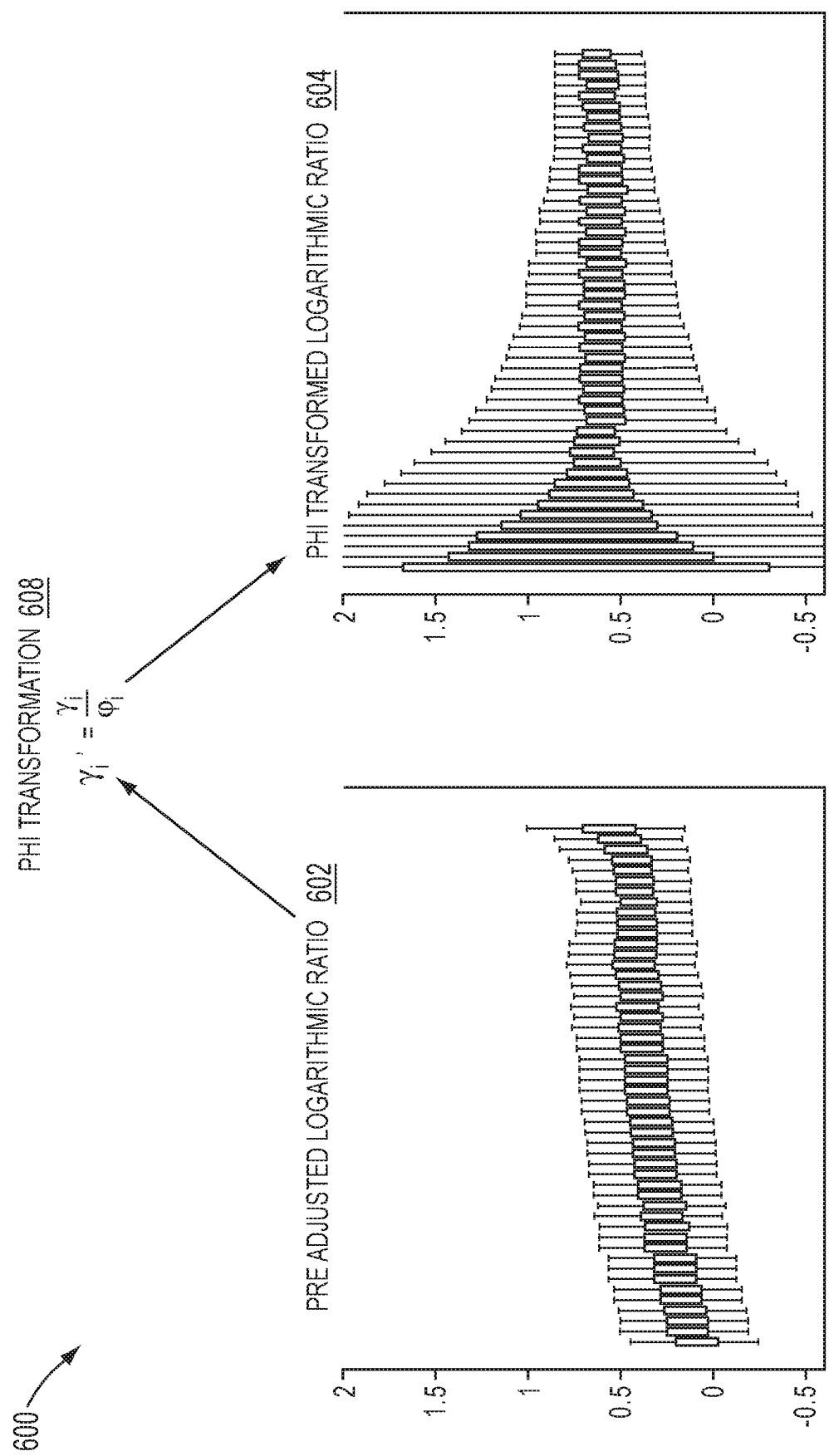
FIG. 6 illustrates a phi transformation 600 in accordance with one embodiment.

Referring to FIG. 6, an exemplary phi transformation 600 according to some embodiments comprises a pre adjusted logarithmic ratio 602, a phi transformed logarithmic ratio 604, and a phi transformation 606.

In some embodiments, the phi transformation 606 is applied to a pre adjusted logarithmic ratio 602 within a known copy number 3 region stratified by slope, transforming the pre adjusted logarithmic ratio 602 into a phi transformed logarithmic ratio 604.

Figure 7:
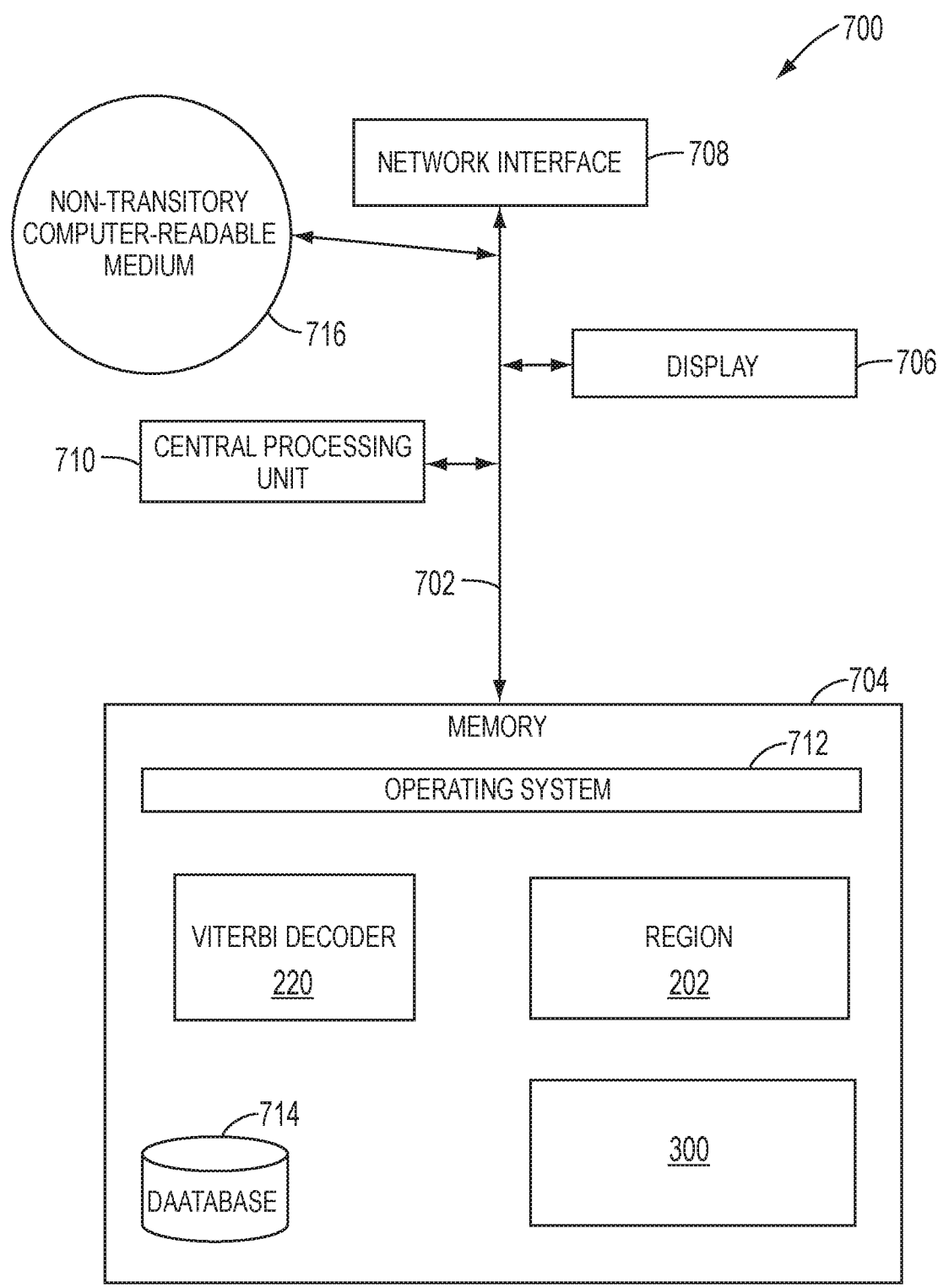
FIG. 7 illustrates an analytic system 700 in accordance with one embodiment.

FIG. 7 illustrates several components of an exemplary system 700 in accordance with one embodiment. In various embodiments, system 700 may include a desktop PC, server, workstation, mobile phone, laptop, tablet, set-top box, appliance, or other computing device that is capable of performing operations such as those described herein. In some embodiments, system 700 may include many more components than those shown in FIG. 7. However, it is not necessary that all of these generally conventional components be shown in order to disclose an illustrative embodiment. Collectively, the various tangible components or a subset of the tangible components may be referred to herein as "logic" configured or adapted in a particular way, for example as logic configured or adapted with particular software or firmware.

In various embodiments, system 700 may comprise one or more physical and/or logical devices that collectively provide the functionalities described herein. In some embodiments, system 700 may comprise one or more replicated and/or distributed physical or logical devices.

In some embodiments, system 700 may comprise one or more computing resources provisioned from a "cloud computing" provider, for example, Amazon Elastic Compute Cloud ("Amazon EC2"), provided by Amazon.com, Inc. of Seattle, Wash.; Sun Cloud Compute Utility, provided by Sun Microsystems, Inc. of Santa Clara, Calif.; Windows Azure, provided by Microsoft Corporation of Redmond, Wash., and the like.

System 700 may include a bus 702 interconnecting several components including a network interface 708, a display 706, a central processing unit 710, and a memory 704.

Memory 704 generally comprises a random access memory ("RAM") and permanent non-transitory mass storage device, such as a hard disk drive or solid-state drive. Memory 704 stores an operating system 712.

These and other software components may be loaded into memory 704 of system 700 using a drive mechanism (not shown) associated with a non-transitory computer-readable medium 716, such as a DVD/CD-ROM drive, memory card, network download, or the like.

Memory 704 may also include database 714. In some embodiments, system 700 may communicate with database 714 via network interface 708, a storage area network ("SAN"), a high-speed serial bus, and/or via the other suitable communication technology.

In some embodiments, database 714 may comprise one or more storage resources provisioned from a "cloud storage" provider, for example, Amazon Simple Storage Service ("Amazon S3"), provided by Amazon.com, Inc. of Seattle, Wash., Google Cloud Storage, provided by Google, Inc. of Mountain View, Calif., and the like.

Terms used herein should be accorded their ordinary meaning in the relevant arts, or the meaning indicated by their use in context, but if an express definition is provided, that meaning controls.

"Circuitry" in this context refers to electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), or circuitry forming a communications device (e.g., a modem, communications switch, or optical-electrical equipment).

"Firmware" in this context refers to software logic embodied as processor-executable instructions stored in read-only memories or media.

"Hardware" in this context refers to logic embodied as analog or digital circuitry.

"Logic" in this context refers to machine memory circuits, non transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter).

"Programmable device" in this context refers to an integrated circuit designed to be configured and/or reconfigured after manufacturing. The term "programmable processor" is another name for a programmable device herein. Programmable devices may include programmable processors, such as field programmable gate arrays (FPGAs), configurable hardware logic (CHL), and/or any other type programmable devices. Configuration of the programmable device is generally specified using a computer code or data such as a hardware description language (HDL), such as for example Verilog, VHDL, or the like. A programmable device may include an array of programmable logic blocks and a hierarchy of reconfigurable interconnects that allow the programmable logic blocks to be coupled to each other according to the descriptions in the HDL code. Each of the programmable logic blocks may be configured to perform complex combinational functions, or merely simple logic gates, such as AND, and XOR logic blocks. In most FPGAs, logic blocks also include memory elements, which may be simple latches, flip-flops, hereinafter also referred to as "flops," or more complex blocks of memory. Depending on the length of the interconnections between different logic blocks, signals may arrive at input terminals of the logic blocks at different times.

"Software" in this context refers to logic implemented as processor-executable instructions in a machine memory (e.g. read/write volatile or nonvolatile memory or media).

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

Various logic functional operations described herein may be implemented in logic that is referred to using a noun or noun phrase reflecting said operation or function. For example, an association operation may be carried out by an "associator" or "correlator". Likewise, switching may be carried out by a "switch", selection by a "selector", and so on.

Those skilled in the art will recognize that it is common within the art to describe devices or processes in the fashion set forth herein, and thereafter use standard engineering practices to integrate such described devices or processes into larger systems. At least a portion of the devices or processes described herein can be integrated into a network processing system via a reasonable amount of experimentation. Various embodiments are described herein and presented by way of example and not limitation.

Those having skill in the art will appreciate that there are various logic implementations by which processes and/or systems described herein can be effected (e.g., hardware, software, or firmware), and that the preferred vehicle will vary with the context in which the processes are deployed. If an implementer determines that speed and accuracy are paramount, the implementer may opt for a hardware or firmware implementation; alternatively, if flexibility is paramount, the implementer may opt for a solely software implementation; or, yet again alternatively, the implementer may opt for some combination of hardware, software, or firmware. Hence, there are numerous possible implementations by which the processes described herein may be effected, none of which is inherently superior to the other in that any vehicle to be utilized is a choice dependent upon the context in which the implementation will be deployed and the specific concerns (e.g., speed, flexibility, or predictability) of the implementer, any of which may vary. Those skilled in the art will recognize that optical aspects of implementations may involve optically-oriented hardware, software, and or firmware.

Those skilled in the art will appreciate that logic may be distributed throughout one or more devices, and/or may be comprised of combinations memory, media, processing circuits and controllers, other circuits, and so on. Therefore, in the interest of clarity and correctness logic may not always be distinctly illustrated in drawings of devices and systems, although it is inherently present therein. The techniques and procedures described herein may be implemented via logic distributed in one or more computing devices. The particular distribution and choice of logic will vary according to implementation.

The foregoing detailed description has set forth various embodiments of the devices or processes via the use of block diagrams, flowcharts, or examples. Insofar as such block diagrams, flowcharts, or examples contain one or more functions or operations, it will be understood as notorious by those within the art that each function or operation within such block diagrams, flowcharts, or examples can be implemented, individually or collectively, by a wide range of hardware, software, firmware, or virtually any combination thereof. Portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more processing devices (e.g., as one or more programs running on one or more computer systems), as one or more programs running on one or more processors (e.g., as one or more programs running on one or more microprocessors), as firmware, or as virtually any combination thereof, and that designing the circuitry or writing the code for the software or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory.

What is claimed is:

1. A discrete region-based calling method, comprising:
receiving a region delineated by a chromosome, a start marker and an end marker and for each marker within the region:
dividing a logarithmic ratio for the marker by an expected responsiveness to copy number change to generate a phi-transformed logarithmic ratio;
modeling a probability distribution of the phi-transformed logarithmic ratio in one or more of states by calculating an emission probability for each of the states;
translating a local path window across the marker to determine a set of possible transition paths through the states and the markers;
constructing a local evidence matrix, for each of the markers, comprising a level of evidence for each of the states based on observed data;
operating a Viterbi decoder with a transition matrix, the local evidence matrix and a state initial probability vector to generate a state vector comprising the state associated with each of the markers along the most probable path through the local evidence matrix;
operating a first segmenter with the state vector to partition segments into a segmentation table of contiguous markers with the same state;
operating a second segmenter with the segmentation table and a minimum segment size to merge segments below the minimum segment size into adjoining segments to produce a minimized segmentation table;
operating a segmentation finalizer on the minimized segmentation table to convert segment indexes to genomic positions; and
summarizing the phi-transformed logarithmic ratio within each segment using the segment's median; and
generating a total per-marker value for each segment.

2. The method of claim 1 wherein the transition matrix is symmetric and a probability of remaining in the same state is higher than transitioning to a different state.

3. The method of claim 1, wherein the state initial probability vector further comprises the initial probability of the marker being in each of the states.

4. The method of claim 1, wherein a length of the local path window is one less than twice a length of each segment.

5. The method of claim 1, wherein dimensions of the local evidence matrix are controlled by the states for rows and the markers for columns.

6. The method of claim 1, wherein calculating the emission probability for each of the states further comprises subtracting a mean for the state from the phi-transformed logarithmic ratio and dividing by a variability estimate of the marker for the state.

7. The method of claim 1, wherein the logarithmic ratio includes a log 2 ratio.

8. The method of claim 1, wherein the logarithmic ratio is a logarithm of an intensity of a specific probe set on an array divided by a reference intensity.

9. The method of claim 8, wherein the reference intensity is an average intensity of intensities observed for the specific probe set from different arrays, where the different arrays are hybridized to nucleic acid populations derived from different individuals.

10. The method of claim 8, wherein the specific probe set includes a set of probes configured to hybridize to a same genomic or transcriptomic locus.

* * * * *